United States Patent
Myles et al.

(10) Patent No.: US 7,541,187 B2
(45) Date of Patent: Jun. 2, 2009

(54) METHOD OF PROVIDING A SUBSTRATE WITH A READY-TO-USE, UNIFORMLY DISTRIBUTED EXTRACELLULAR MATRIX

(75) Inventors: Arthur Myles, Hingham, MA (US); Stephen R. Ilsley, Boston, MA (US); Frank J. Mannuzza, Chelmsford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 199 days.

(21) Appl. No.: 10/164,486

(22) Filed: Jun. 6, 2002

(65) Prior Publication Data

US 2002/0197718 A1 Dec. 26, 2002

Related U.S. Application Data

(60) Provisional application No. 60/296,407, filed on Jun. 6, 2001.

(51) Int. Cl.
C12N 5/00 (2006.01)
C12N 5/02 (2006.01)
A01N 63/00 (2006.01)

(52) U.S. Cl. .............. 435/395; 435/320.1; 435/382; 435/397

(58) Field of Classification Search ............. 435/70.1, 435/366, 368, 371, 395
See application file for complete search history.

(56) References Cited

U.S. PATENT DOCUMENTS

| | | | |
|---|---|---|---|
| 3,393,080 A * | 7/1968 | Ferraro et al. ............ 530/356 |
| 4,829,000 A | 5/1989 | Kleinman et al. |
| 4,970,298 A * | 11/1990 | Silver et al. ............ 530/356 |
| 5,354,666 A | 10/1994 | Danielson et al. |
| 5,629,191 A | 5/1997 | Cahn |
| 5,731,417 A | 3/1998 | Swiderek et al. |
| 5,741,701 A * | 4/1998 | Swiderek et al. ......... 435/297.1 |
| 5,755,814 A * | 5/1998 | Berg et al. ............... 623/66.1 |
| 5,800,537 A | 9/1998 | Bell |
| 5,817,764 A | 10/1998 | Swiderek et al. |
| 5,874,099 A * | 2/1999 | Dionne et al. ............. 424/422 |
| 5,891,558 A | 4/1999 | Bell et al. |
| 5,958,874 A * | 9/1999 | Clark et al. ................. 514/2 |
| 5,965,125 A | 10/1999 | Mineau-Hanschke |
| 5,985,539 A | 11/1999 | Takezawa et al. |
| 7,195,912 B2 * | 3/2007 | Takezawa et al. ............ 435/397 |

FOREIGN PATENT DOCUMENTS

| | | |
|---|---|---|
| JP | 06-054899 | 1/1994 |
| JP | 08-228768 | 9/1996 |
| JP | 11-319068 | 11/1999 |

OTHER PUBLICATIONS

Menicon Co. Ltd., Machine Translation of JP 11-319068—Complete Document,. Issued Nov. 24, 1999.*
Technical Bulletin #427, An Improved MATRIGEL® Invasion Chamber, Ilsley et al., Becton Dickinson and Company, 1998.
BD Matrigel™ Basement Membrane Matrix, www.bdbiosciences.com., Becton, Dickinson and Company, 2002.

* cited by examiner

*Primary Examiner*—Jon P Weber
*Assistant Examiner*—Kailash C Srivastava
(74) *Attorney, Agent, or Firm*—Hoffmann & Baron, LLP

(57) ABSTRACT

Method of providing a substrate with a ready-to-use uniformly distributed extracellular matrix is disclosed. This method includes applying extracellular matrix components to a substrate area; incubating the extracellular matrix components to allow polymerization thereof; freezing the polymerized extracellular matrix on the substrate area; lyophilizing the frozen extracellular matrix on the substrate area; and allowing the lyophilized extracellular matrix to warm to room temperature. Also contemplated is a cell culture apparatus having a dried uniformly distributed extracellular matrix formed by the above-mentioned method.

9 Claims, No Drawings

METHOD OF PROVIDING A SUBSTRATE WITH A READY-TO-USE, UNIFORMLY DISTRIBUTED EXTRACELLULAR MATRIX

This application claims the benefit of U.S. Provisional Application No. 60/296,407, filed on Jun. 6, 2001.

BACKGROUND OF THE INVENTION

1. Field of Invention

The present invention relates generally to a method of providing a unique cell culture medium. More particularly, this invention relates to a method of extracting fluid from a cell culture apparatus that includes a uniformly distributed extracellular matrix adhered to a substrate.

2. Background of Related Technology

The network of fibrous and globular proteins lying between cells is called the extra-cellular matrix (ECM). ECM is a vital component of the cellular environment. Various ECM components are secreted by cells to form an interstitial matrix and basement membrane, the framework to which cells are anchored in vivo. These structures provide spatial orientation and the stability required for the organization and development of tissue-specific histology. However, the ECM is not merely an inert scaffolding, but an essential player in the regulation of the cell growth and differentiation. The ECM provides a milieu which plays a pivotal role in regulating cellular functions during normal pathological remodeling processes such as embryonic development, tissue repair, inflammation, tumor invasion, and metastasis. For example, ECM is known to function in the induction, sequestration, storage and presentation of growth factors.

In recognition of the fact that ECM is a vital component of the cellular micro environment, more and more researchers are incorporating extracellular matrix into their cell culture systems. In vitro use of ECM provides cells with conditions which more closely approximate their in vivo physiologic environments. ECM provides cells with mechanical support and influences their behavior by providing biochemical cues that affect cells via cell surface receptors.

The basement membrane is a specific type of extracellular matrix and is composed primarily of laminin and type IV collagen. A well-known Basement Membrane Matrix extracted from the Engelbreth-Holm-Swarm mouse tumor, is sold under the brand name MATRIGEL®. The terms MATRIGEL®, MATRIGEL® Matrix, and the like, as used herein refer to BD MATRIGEL® Basement Membrane Matrix (Becton, Dickinson and Co.), a mixture of basement membrane proteins derived from the Engelbreth-Holm-Swarm mouse tumor. This mouse tumor is rich in basement membrane proteins. The major matrix components are laminin, collagen IV, entactin and heparan sulfate proteoglycan and also contains growth factors, matrix metalloproteinases (MMPs [collagenases]), and other proteinases (plasminogen activators), as well as several undefined compounds, but it does not contain any detectable levels of tissue inhibitors of metalloproteinases (TIMPs). At room temperature, MATRIGEL® Matrix gels to form reconstituted basement membrane and is similar in its structure, composition, physical property and ability to retain functional characteristics typical of basement membranes in vivo.

A number of methods have been developed using MATRIGEL® Matrix to investigate the invasion of the basement membrane matrix by tumor cells, in vitro. Typically these methods involve the coating of MATRIGEL® Matrix onto the microporous membranes of cell culture inserts. Conventional techniques to prepare an ECM containing cell culture system include, first, warming a cold, neutralized solution of soluble collagen to induce polymerization and precipitation of native fibrils. Incubating the MATRIGEL® Matrix at a raised temperature of over 4° C. polymerizes the matrix.

Whereas amorphous, chemically cross-linked and alkali denatured collagen films for use in cell cultures are often dried to improve shelf life and to eliminate the need to prepare the cell culture substrate prior to each use, cell culture substrates containing native fibrillar collagen are prepared and used only in the form of firm, adherent gels of native fibrils. These gels are most often produced, as mentioned above, by warming a cold, neutralized solution of soluble collagen to induce polymerization and precipitation of native fibrils. However, they are not dried for storage because previous attempts to collapse and dry the native fibrillar collagen gels have resulted in the loss of native structure, suboptimal fiber formation and poor permeability characteristics. Native fibrillar collagen cell culture substrates must, therefore, be made just prior to use. This increases the labor and inconvenience associated with studies involving cell cultures with native fibrillar collagen. Thus, there exists a need for a cell culture substrate that contains a native fibrillar collagen, such as those found in MATRIGEL® Matrix, that can be prepared from a manufacture well before their intended use.

Conventional methods of preparing a cell culture apparatus containing native fibrillar collagen desirably remove fluid residing in the matrix just prior to use and after the gel is polymerized. Conventional methods to remove the fluid from an ECM include air drying and drying at elevated temperatures. Common elevated drying conditions include rapid drying at elevated temperatures with a drying airflow which promote large salt crystals and more pronounced patterning of the MATRIGEL® Matrix. Rapid drying of the MATRIGEL® Matrix results in poor distribution of the invading cells.

Conventional fluid removing techniques also include placing the underside of the porous surface on an absorbent material for a period of 3 minutes to overnight and/or applying a gentle vacuum to the underside of the porous surface. Fluid removed by slow drying under conditions of slowly decreasing temperature and without airflow resulted in the most even coating and, thus, the most even distribution of invading cells. For example, Swiderek, et al (U.S. Pat. No. 5,731,417) discloses methods of making dried films of native fibrillar collagen for cell culture which includes air drying the substrates.

Conventional drying methods degrade the functionality of the cell culture apparatus. For example, conventional coating and drying methods often result in an uneven or disrupted coating which gives rise to uneven cell invasion manifested by the formation of the various patterns such as intense central dots or rings of invading cells. As a result, the accurate counting of invading cells under the microscope is greatly complicated. Additionally, the ability to discriminate between invasive and non-invasive cells is significantly diminished. Invasive cells include HT-1080 cells and non-invasive cells include NIH 3T3 cells. Therefore, a distributed fibrillar collagen substrate, such as a MATRIGEL® matrix, is desirably uniform and consistent.

SUMMARY OF INVENTION

This invention relates to a cell culture apparatus and method that includes a dried extracellular matrix and has been developed for the in vitro growth of cells. In particular, this invention contemplates a method of providing a substrate with a ready-to-use uniformly distributed extracellular matrix including a) applying extracellular matrix components to a substrate area; b) incubating the extracellular matrix components to allow polymerization thereof; c) freezing the polymerized extracellular matrix on the substrate area; d) lyophilizing the frozen extracellular matrix on the substrate area; e) allowing the lyophilized extracellular matrix to warm to room temperature.

Another aspect of this invention provides a cell culture apparatus including a surface intended for cell growth, said surface having attached thereto a dried uniformly distributed extracellular matrix, said matrix formed by the steps including a) applying extracellular matrix components to a substrate area; b) incubating the extracellular matrix components to allow polymerization thereof; c) freezing the polymerized extracellular matrix on the substrate area; d) lyophilizing the frozen extracellular matrix on the substrate area; e) allowing the lyophilized extracellular matrix to warm to room temperature.

The invention also provides a cell culture apparatus including a surface adapted to grow cells thereon; and an extracellular matrix coating on the surface, the matrix coating comprising the polymerization product of a solution of bioactive proteins, wherein fluid residing within the matrix is substantially removed through lyophilization.

The present invention attempts to solve the deficiencies of the prior art by describing a method that provides a cell culture apparatus which contains an extracellular matrix that has a uniform distribution, is effective over a wider range of ECM concentrations, gives a highly uniform tumor cell migration over the entire cell culture surface, facilitates counting of cells, differentiates between invasive tumor cells and supposedly non-invasive control cells. Additionally, the present invention also includes cell culture apparatus that includes an extracellular matrix prepared well in advance of its intended use.

DETAILED DESCRIPTION OF INVENTION

The present invention provides a highly uniform extracellular matrix coating from edge to edge of a substrate and is effective over a significantly wider range of extracellular matrix concentrations than those prepared by conventional liquid drying processes. The uniformity of the coating gives a highly uniform tumor cell migration over the entire extracellular matrix surface as opposed to the conventional process where cell migration takes place in a very uneven manner at the center of the membrane. The uniform migration facilitates counting of the cells by either manual methods or by image analysis. The lyophilized coating also has a great ability to differentiate between invasive tumor cells and supposedly non-invasive control cells.

A cell culture apparatus having dried native fibrillar collagen may be substituted for conventional collagen cell culture substrates in any of the cell culture protocols and methods known in the art. The native fibrillar collagen cell culture substrate on the porous surface is placed in the well of a tissue culture plate with the underside of the porous surface in contact with an appropriate culture medium. This allows the culture medium to flow through the porous surface into contact with the cell culture substrate. The culture medium and other materials which may be present in it diffuse through the cell culture substrate into contact with cells seeded on its surface. For ease of handling, the cell culture substrate may be prepared on the microporous membrane of a cell culture insert.

Upon application of a cold extracellular matrix to a porous surface, the temperature of the cold, neutralized collagen solution is allowed to increase to about 15° C. to about 40° C. to initiate native collagen fibril and fiber formation. For the incubation step of the present invention, temperatures desirably are elevated, preferably about 37° C., with about 5% carbon dioxide in a humidified chamber. As the temperature of the collagen solution increases, native fibrils begin to polymerize and gel on the porous surface, coating the upper side thereof. The gel comprises large, organized fibers of collagen with the striations characteristic of native collagen as well as entrapped fluid from the collagen solution (interfibril fluid). Desirably, the incubation step would be an amount of time sufficient for the extracellular matrix to form a gel. The incubation step may be conducted in the presence of carbon dioxide. In general, about 0.5 to about 3 hours at about 37° C. is sufficient to obtain complete polymerization on a porous surface such as the membrane of a cell culture insert.

After the collagen of the extracellular matrix is polymerized, the interfibril fluid of the polymerized collagen is desirably drawn out of the gel. The method of the present invention directs the gel coated inserts to be frozen at a temperature no warmer than −30° C. prior to initiating the lyophilization process. Coated inserts may be frozen in a lyophilizer and then lyophilized overnight during which time the lyophilizer is allowed to warm to room temperature. This process collapses the gel onto the porous surface and forms a thin membrane of native collagen fibers and fibrils. Desirably a uniform cake is obtained which adheres to the insert membrane.

The native fibrillar collagen cell culture substrates of this invention may be produced as dried films on porous surfaces. They desirably retain the native fibrillar collagen structure in dried form and therefore have the improved permeability characteristics of cast collagen gels and the storage stability of amorphous or cross-linked collagen films. The dried membrane may be removed from the porous surface for cell culture if desired, but it is generally preferable to use the native fibrillar collagen cell culture substrate on its porous surface for added structural support and ease of handling. Cells on the upper surface of the cell culture substrate may be exposed to media, growth factors, and other materials by diffusion thereof through the underside of the porous surface and the cell culture substrate, as the cell culture films of the invention exhibit excellent diffusion properties.

Salt concentrations which are at about physiologic concentrations or higher, preferably about 0.15 Molar to about 1 Molar, may be used to promote formation of large native collagen fibers. At salt concentrations below physiologic concentrations there is little, if any, collagen fiber formation. However, as salt is increased to approximately physiologic concentrations, fiber formation becomes essentially complete, with little amorphous collagen being present. Additionally, as salt is increased above physiologic concentrations, larger and larger fibers are formed. However, when the salt concentration reaches about 1.1 Molar, fiber formation is again essentially completely absent. When the solubilized collagen is in acidic solution, the pH may be raised to approximately 6-8, preferably about 7.0-7.4, concurrently with adjustment of the salt concentration by addition of cold NaOH in a buffer such as phosphate buffered saline (PBS) to give a final salt concentration of about 0.15 Molar-1 Molar, preferably at least about 0.6 Molar (about 4 times physiologic salt). The collagen is maintained in solution by storage in the cold (usually about 4° C.) until polymerization of collagen fibrils and fibers is desired. The collagen concentration is not critical for formation of the native collagen fibers, but is preferably about 10 to about 500 μg/cm$^2$ of porous surface when intended for use as a cell culture substrate, more preferably about 65 to about 85 μg/cm$^2$.

A variety of polymerization conditions, including non-physiological conditions, may be used to produce the cell culture films without concern for negative effects of non-collagenous residuals such as salts or organic materials on the cell environment. Collapsing the gel onto the porous surface and drying, in accordance with the method of this invention, to form the fibrillar collagen film provides a uniform surface for even distribution of cells and if desired, a concentration of collagen (about 5-10 mg/ml). The native fibrillar collagen structure provides the in vivo spatial orientation for binding of cell receptors not found in amorphous collagen cell culture substrates. The fibrillar collagen network also provides a textured surface which results in a higher collagen surface area on each film than is found on the essentially two-dimensional surfaces of other collagen cell culture substrates. The native fibrillar collagen cell culture substrates bind cells more avidly and uniformly to their surfaces than do the collagen substrates of the prior art. That is, many diverse cell types applied to the surface bind to it rapidly and completely (e.g., epithelial cells, endothelial cells and fibroblasts).

Organizational entropy drives the polymerization reaction of the invention. As the physical mechanism is the same for other proteins which undergo a similar type of self-assembly, any protein or proteins which spontaneously form organized polymeric structures in vitro will produce native constructs when substituted for collagen in the foregoing production process. These include proteins which form homopolymers (e.g., fibronectin or laminin) and heteropolymers (e.g., laminin with collagen IV or laminin with proteoglycans). Extracellular matrix components which comprise proteins which undergo self assembly, such as those found in MATRIGEL® (Collaborative Biomedical Products, a company of Becton, Dickinson and Co.), may be polymerized and dried according to the methods of the invention to produce native constructs. Although all such proteins may not produce gels which collapse and form a film in the same manner as collagen gels when the interfibril fluid is removed, withdrawal of the interfibril fluid from the polymerized substrate and drying should still allow retention of the native construct in the final product.

Any membrane material may be used as the substrate with the method of the invention, however, there may be positive or negative effects of the selected membrane in certain biological applications. Whereas, etched membranes may be preferred for transport studies, cast membranes may also be used if the permeability coefficient of the material being tested does not exceed the permeability coefficient of the membrane (i.e., the permeability coefficient of the membrane is not a limiting factor). For convenience in cell culture applications, culture plate inserts which incorporate porous membranes may be preferred. For example, suitable substrates include BIOCOAT control cell culture inserts, which are porous polyethylene terephthalate membranes available from Collaborative Biomedical Products. Other suitable substrates included TRANSWELL cell culture inserts, which are porous polycarbonate membranes available from Costar. Further suitable substrates are MILLICELL Culture Plate Inserts, which are porous polytetrafluoroethylene membranes, porous cellulose membranes, or porous polycarbonate membranes available from Millipore Corporation. Polyethylene terephthalate (PET) membranes may be preferred over materials such as high density polycarbonate for applications involving microscopy due to their higher transparency. For these reasons, different membranes may therefore be preferred for different applications and can be routinely selected by one skilled in the art.

Suitable porous surfaces to be used as the substrate of the present invention include natural or synthetic polymers such as cellulose membranes, porous polycarbonate, porous polytetrafluoroethylene (e.g., TEFLON mesh membranes such as Millipore CM), nylon membranes and meshes, glass filters, porous polyethyleneterephthalate, polymethylpentane, polyproplyene, polyethylene and various types of filters (e.g., ANOPORE aluminum crystal filters). The porous surface should have a pore size which is small enough to prevent the collagen solution from flowing though prior to polymerization but large enough to allow passage of fluids such as media and the interfibril fluid. In general, membranes having pore sizes of about 0.5 to about 30 microns provide the desired properties. A surface comprising a membrane with pores approximately 8 microns is preferred for most general cell culture applications such as material transport studies.

After drying, the cell culture apparatus of the present invention may be sterilized, for example by irradiation (e.g., ultraviolet light, electron beam or gamma irradiation) or exposure to ethylene oxide gas. The native fibrillar collagen films of the invention, in contrast to the collagen cell culture substrates of the prior art, retain their native fibrillar structure when dried and therefore more closely resemble an in vivo collagen substrate.

A wide variety of materials, including bioactive proteins, may be co-polymerized with the extracellular matrix of the present invention or incorporated into the film by adsorption to the collagen, as desired for a particular cell culture system. These include, but are not limited to, cells, antibodies, enzymes, receptors, growth factors, additional components of the extracellular matrix, cytokines, hormones and drugs. These materials may be added to the cold collagen solution at the appropriate concentration for the selected cell culture application. Polymerization of the native collagen fibrils as described above binds the material to or copolymerizes the material with the collagen fibers. Due to the open fiber structure of the cell culture substrate, biologically active added materials are readily available to the cultured cells to moderate or regulate their properties or behavior.

The cells to be cultured may be seeded at subconfluence or confluence on the upper surface of the substrate and placed under environmental conditions appropriate for cell growth. For example, when the cell culture substrate is prepared on the surface of the membrane of an insert for the well of a culture dish, a small amount of growth medium is placed in the well. The insert is placed in the well so that the culture medium contacts the underside of the porous membrane and diffuses through the cell culture substrate into contact with cells seeded on the substrate surface.

Any cell culture medium appropriate for growth and differentiation of epithelial cells may be used in cell cultures employing the present collagen cell culture substrates. These include, but are not limited to Dulbecco's Modified Eagle Medium (DMEM), MEM, M-199 and RPMI. Supplements, as are known in the art, may be added to the culture medium and include serum (e.g., fetal bovine serum (FBS) or calf serum), serum-containing supplements (NU-SERUM), and serum-free supplements (MITO+). A preferred cell culture medium for intestinal epithelial cells is DMEM supplemented with MITO+ Serum Extender (Collaborative Biomedical Products, Bedford, Mass.) to provide a fully defined, serum-free cell culture environment.

The following examples are given to illustrate certain embodiments of the invention and are not to be construed as limiting the invention as defined by the appended claims and equivalents thereof.

EXAMPLE 1

Preparation of a Cell Culture Apparatus Having a Dried Uniformly Distributed Extracellular Matrix The following experimental example describes the preparation of dried uniformly distributed native fibrillar collagen cell culture substrates on 1 μm polyethyleneterephthalate (PET) membranes in PET cell culture inserts. In this example, about 200 μm of MATRIGEL® Matrix is added to the membrane.

A cold acid solution of MATRIGEL® Matrix is adjusted to 674 μm/ml by addition of 10 times Dulbecco's phosphate buffered saline (DPBS)/NaOH to obtain a final concentration of about 4 times DPBS, pH 7.4, and the mixture is kept on ice until use. Insert holders are placed in tissue culture dishes. The cell culture inserts are placed in the insert holders with sterile forceps and lids are placed on the dishes until use. The MATRIGEL® collagen coating gel (0.10 ml) is dispensed onto each membrane, the culture dish lid is replaced and the dish is rocked gently to evenly distribute the coating solution on the membrane. The coated membranes are incubated at 37° C. to allow the collagen to polymerize (about 2.0 hrs.), keeping the membranes in a humid environment to prevent premature drying.

After the collagen is polymerized, the coated inserts are placed in a pre-chilled lyophilizer and frozen (at a temperature no warmer than –30° C.) prior to initiating the lyophilization process. Inserts are lyophilized overnight during which time the lyophilizer is allowed to warm to room temperature. A uniform cake is obtained which adheres to the insert membrane.

The native collagen cell culture substrates are then sterilized in the tissue culture dishes by exposure to 0.05-0.06 Joules of ultraviolet light and are stored at 4 degree C. in sealed bags until use.

EXAMPLE 2

Invasion Assay

NIH 3T3 (non-invasive) and HT-1080 (invasive) cells were grown to near confluence in DMEM containing 10% fetal bovine or newborn calf serum. The cells were harvested by trypsinization and washed in DMEM without adding serum or proteinase inhibitor. The cells were suspended in DMEM at $1 \times 10^5$/ml. Prior to preparing the cell suspension, the dried layer of MATRIGEL® Matrix was rehydrated with DMEM for 2 hours at room temperature. The rehydration solution was carefully removed, 0.75 ml DMEM containing 5% fetal bovine serum was added to each plate well as a chemoattractant, and 0.5 ml ($5 \times 10^4$ cells) of cell suspension was added to each insert. The plate inserts were incubated for 22 hours at 37° C., 5% $CO_2$ atmosphere. Non-coated membrane inserts were also seeded to serve as controls.

Fixation and Staining of Coated Inserts

Following incubation, the upper surface of the membrane in each insert was gently scrubbed with a cotton swab to remove all of the non-invading cells and the MATRIGEL® Matrix. The invading cells on the undersurface of the membrane were fixed and stained by sequentially transferring them through the three solutions of the Diff-Quik (Dade) staining kit. The excess stain was removed by dipping each insert into distilled water. The upper surface of the membrane was swabbed a second time to remove any residual water, cells or MATRIGEL® Matrix. The inserts were transferred to another 24-well plate and allowed to air dry. The number of cells which had invaded through the MATRIGEL® Matrix on the membrane was quantitated on the lower side of the membrane by direct counting in a microscope after the cells had been stained with Diff-Quik.

The cells were enumerated by taking photomicrographs at 40 or 200× magnification depending on the number and distribution of the cells. Photographs were taken without removing the membrane from the insert housing. The cells in multiple fields (usually 5) of each photograph were counted with the aid of a ruled grid. Data was expressed as % invasion, i.e., the ratio of cells invading through the MATRIGEL® Matrix coated inserts relative to the uncoated control insert.

Protein Staining of Coated Inserts

In order to assess the evenness of the distribution of the coat, coated inserts were stained with Coomassie Blue for a profile on the protein content across the insert surface. Coated inserts were rehydrated with buffered saline for 2 hours at room temperature. The rehydration solution was carefully removed and replaced with Coomassie staining solution (1 mg per ml Coomassie Brilliant Blue R-250 in 10% acetic acid, 40% methanol). After 30 minutes, the stain was carefully removed, the inserts were rinsed twice with distilled water and allowed to air dry. The quality of the MATRIGEL® Matrix deposition was assessed at 100× magnification.

EXAMPLE 3

Results of Invasion Assay Employing Inventive Cell Culture Apparatuses

This example demonstrates that cell culture inserts which were prepared in accordance with the methods of the invention performed according to desired performance specifications; these specifications are shown in Table 1 below where NIH 3T3 (3T3) cells are representative of non-invasive tumor cells and HT-1080 cells are representative of metastatic tumor cells.

TABLE 1

| Desired Performance Specifications | | | |
| --- | --- | --- | --- |
| NIH 3T3 Invasion | HT-1080 Invasion | Patterning | Coat Surface Distribution |
| 10% or less | 25% or greater | None | Even |

Inventive cell culture inserts were tested for the ability of NIH 3T3 cells and HT-1080 cells to invade a basement membrane matrix. Fixed and stained inserts were examined as described above to assess the degree of invasion and patterning. The results of these assessments are detailed below.

The inventive cell culture apparatuses showed essentially no invasion of the control NIH 3T3 cells, i.e. the non-invasive cells. There was, however, a high degree of invasion of the HT 1080 tumor cells. Invading HT-1080 cells were evenly distributed across the surface of each insert, providing a highly uniform tumor cell migration over the entire cell culture surface. The inventive cell culture apparatuses were devoid of patterning such as intense central dots or rings of invading cells. The results of the present example were demonstrated with both individual 24 well inserts, as well as the 24 multi well inserts. The thin, even coat of MATRIGEL® Matrix, uniformly spread across the membrane surface by this method, may permit shorter times for completion of tumor invasion assays.

What is claimed is:

1. A method of preparing a cell culture substrate with a uniformly distributed extracellular matrix comprising:
   a) raising the pH of an acidic solution of an extracellular matrix comprising collagen fibrils to 6-8 by the addition of a base;
   b) applying the solution of the extracellular matrix of step a) to a porous substrate area;
   c) polymerizing said applied extracellular matrix on said porous substrate area, wherein said polymerizing comprises incubating said solution at 15° C. to 40° C.;
   d) freezing said polymerized extracellular matrix on said porous substrate area;
   e) lyophilizing said frozen extracellular matrix on said porous substrate area, thereby obtaining a cell culture substrate with a uniformly distributed extracellular matrix.

2. The method according to claim 1, wherein said polymerizing comprises incubating said applied solution of extracellular matrix for 0.5 to 3 hours in the presence of carbon dioxide.

3. The method according to claim 1, wherein said polymerized extracellular matrix is frozen at a temperature no warmer than −30° C.

4. The method according to claim 1, wherein said extracellular matrix further comprises a component selected from the group consisting of laminin, entactin, heparan sulfate proteoglycan, growth factors and combinations thereof.

5. The method according to claim 1, wherein said porous substrate area is a membrane material selected from the group consisting of porous membrane, etched membrane, cast membranes and combinations thereof.

6. The method of claim 1, wherein said porous substrate area includes natural or synthetic polymers selected from the group consisting of cellulose membranes, porous polycarbonate, porous polytetrafluoroethylene, nylon membranes and meshes, glass filters, porous polyethyleneterephthalate, polymethylpentane, polypropylene, polyethylene and combinations thereof.

7. The method according to claim 2, wherein said polymerizing comprises incubating said applied solution of extracellular matrix at a temperature of about 37° C.

8. The method according to claim 2, wherein said carbon dioxide concentration is 5%.

9. The method according to claim 5, wherein said membrane material has pores from about 0.5 to about 30 microns.

* * * * *